United States Patent [19]

Colin et al.

[11] Patent Number: 5,033,650
[45] Date of Patent: Jul. 23, 1991

[54] MULTIPLE BARREL DISPENSING DEVICE

[76] Inventors: Laurence Colin, Box 301, Cross River, N.Y. 10518; Edward R. Spehar, 40 Orion Way, Neshanic Station, N.J. 08853; Bernard F. Harkins, 2000 Woodland Ave., S. Plainfield, N.J. 07080

[21] Appl. No.: 354,311

[22] Filed: Jun. 15, 1989

Related U.S. Application Data

[63] Continuation-in-part of Ser. No. 334,817, Apr. 7, 1989, Pat. No. 4,995,540, which is a continuation of Ser. No. 129,070, Dec. 7, 1987, abandoned, which is a continuation-in-part of Ser. No. 23,838, Mar. 9, 1987, Pat. No. 4,753,536.

[51] Int. Cl.$^5$ .............................................. B67D 5/52
[52] U.S. Cl. ..................................... 222/137; 222/145; 222/459; 222/567; 433/90; 285/361
[58] Field of Search ............... 222/132, 136, 137, 145, 222/276, 386, 459, 490, 567; 433/80, 89, 90; 285/396, 361

[56] References Cited

U.S. PATENT DOCUMENTS

| 245,263 | 8/1881 | Robb | 285/396 |
| 1,193,446 | 8/1916 | Wells | 285/361 |
| 2,198,905 | 4/1940 | Context | 285/361 |
| 3,386,626 | 6/1968 | Kearney | 222/567 |
| 3,799,453 | 3/1974 | Hart | 285/396 |
| 4,538,920 | 9/1985 | Drake | 222/145 |
| 4,708,370 | 11/1987 | Todd | 285/396 |
| 4,767,026 | 8/1988 | Keller et al. | 222/137 |
| 4,771,919 | 9/1988 | Ernst | 222/145 |
| 4,869,400 | 9/1989 | Jacobs | 222/145 |

Primary Examiner—H. Grant Skaggs

[57] ABSTRACT

A multiple barrel device for separate storage of viscous materials and for dispensing and intermixing same through a common static mixing element when pressure is applied. The device includes a multiple barrel syringe and a removable nozzle which is coupled to the syringe to form an interlock and a simultaneous pressure seal. The head of the syringe has a plurality of lugs which form bayonet grooves for engaging a complementary number of tong-like projections extending from the head of the nozzle. The head of the nozzle contains an annular bead which simultaneouly seals the interface at the intercoupling between the head of the syringe and the head of the nozzle.

6 Claims, 3 Drawing Sheets

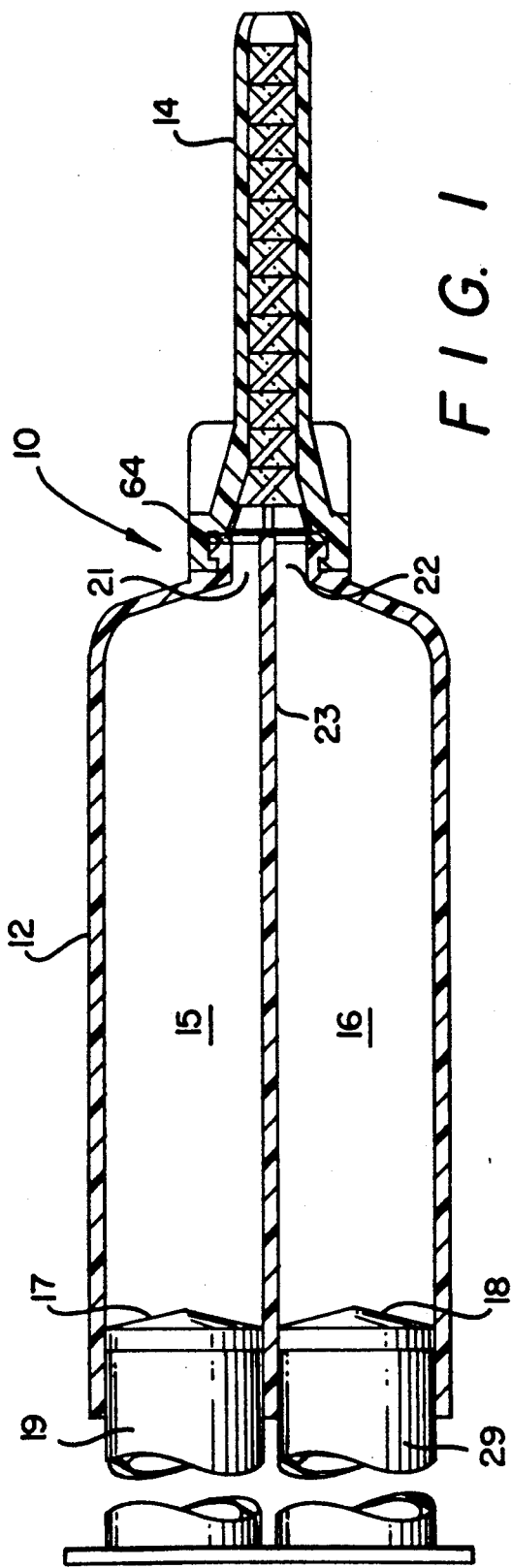
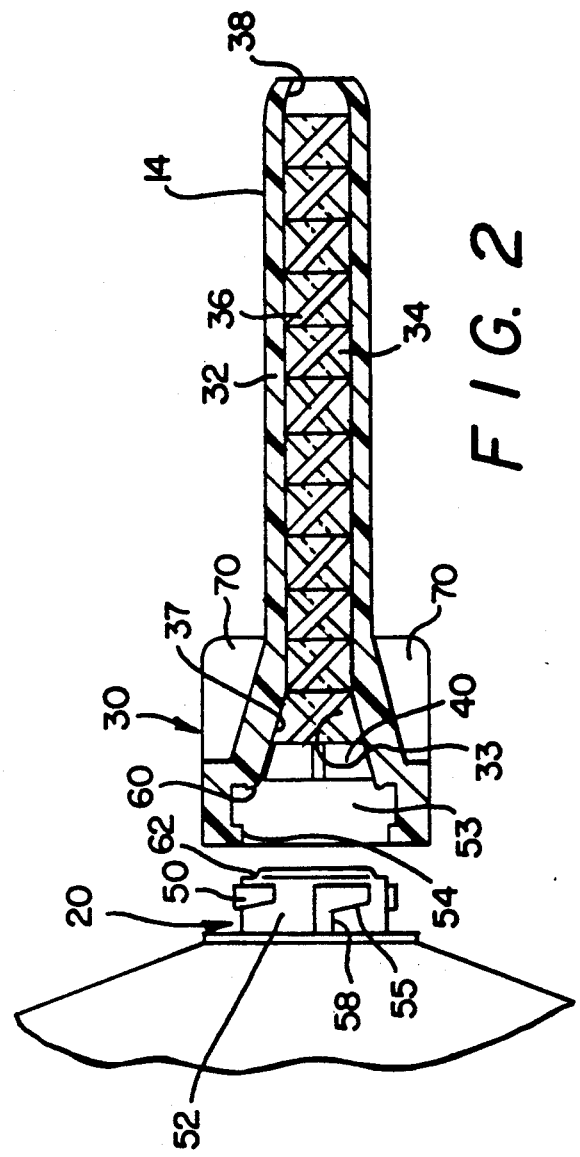

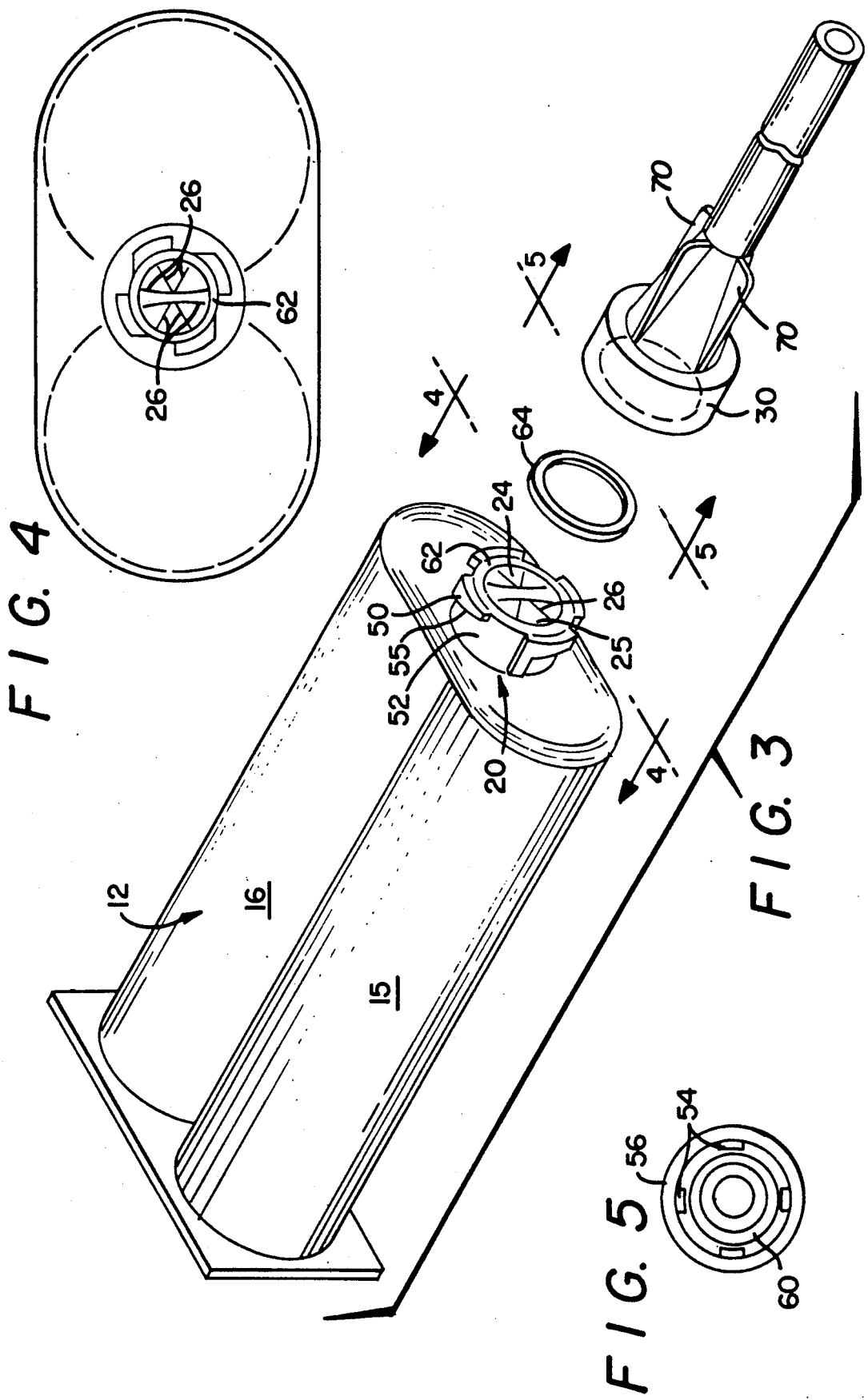

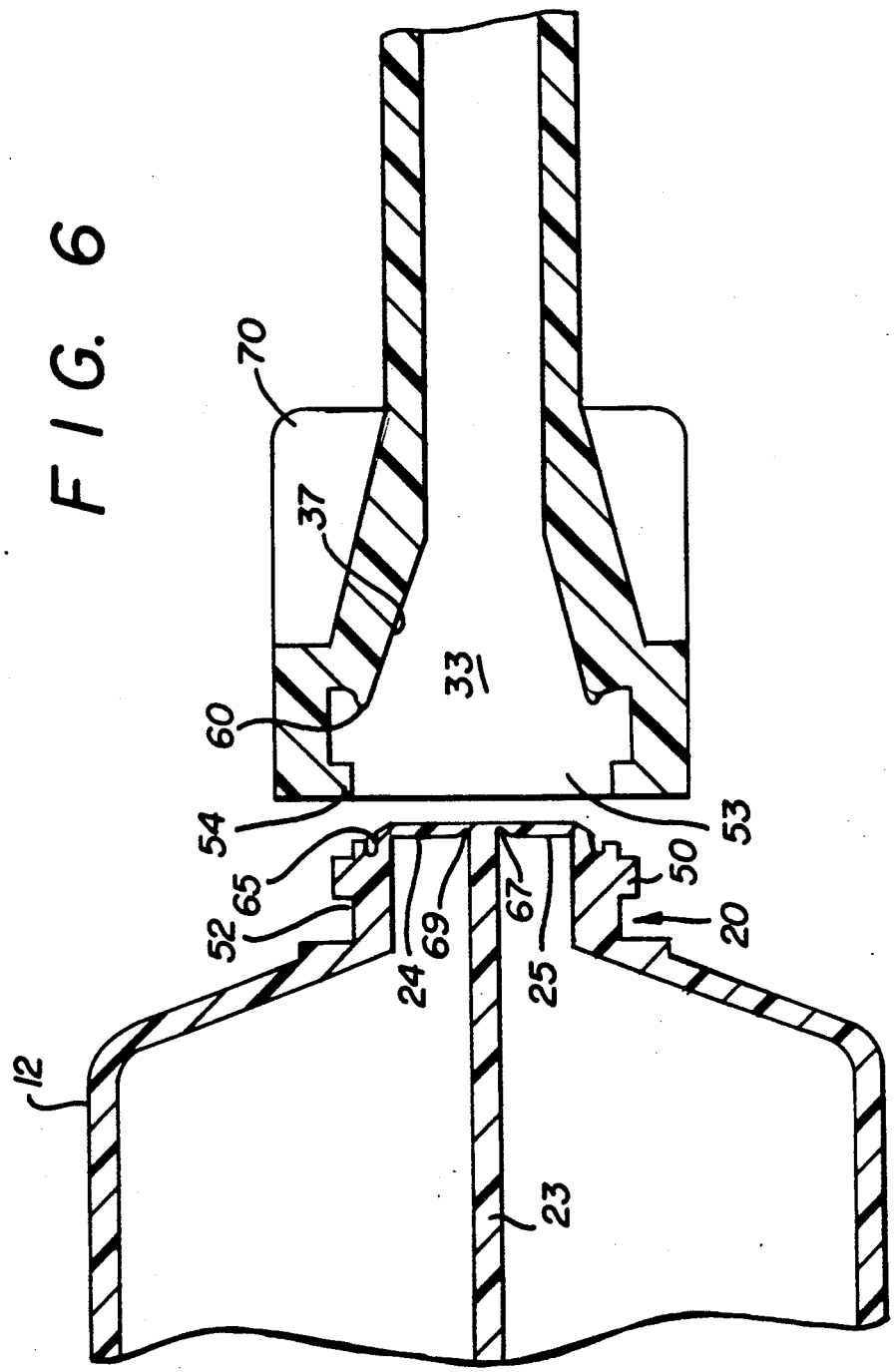

MULTIPLE BARREL DISPENSING DEVICE

"Field of Invention"

This invention is a continuation-in-part of U.S. Ser. No. 334,817, filed Apr. 7, 1989, now Pat. No. 4,995,540 which is a continuation of U.S. Ser. No. 129,070, filed Dec. 7, 1987, now abandoned, which, in turn, is a continuation-in-part of U.S. Ser. No. 023,838, filed Mar. 9, 1987, now U.S. Pat. No. 4,753,536.

BACKGROUND OF THE INVENTION

A hand-held dispensing device for intermixing dental impression materials and for dispensing the mixed product through a common spout is shown and described in U.S. Pat. No. 4,753,536 and 4,538,920, respectively. In general, the prior art dispensing devices broadly consist of a syringe having a multiple barrel cartridge assembly for storing separate materials in individual storage compartments, and a nozzle assembly containing a common mixing element for intermixing the materials fed through the mixing element from their respective storage compartments and a common spout for discharging the mixed product.

Various arrangements for removably coupling the nozzle assembly to the syringe are also described in the prior art. As long as the materials stored in the syringe are of relatively low viscosity so as to require minimal force to feed the materials through the common mixing element in the nozzle assembly, the particular coupling arrangement is of no consequence. However, for materials which are viscous and must be fed under pressure, the coupling arrangement becomes a limiting factor in the design of the dispenser. In the latter case, the removable coupling arrangement must be able to withstand the pressure required to feed the materials through the mixing element in the nozzle assembly, without the nozzle assembly separating from the syringe and without permitting leakage, particularly at the interlock. The coupling must also be inexpensive and simple enough to be readily uncoupled to permit reuse by replacement or substitution of another nozzle. If internal leakage occurs in the coupling area before discharging materials from the syringe into the nozzle assembly, the materials will polymerize and cross-contaminate at the orifice in the head of the syringe preventing use of the dispenser before the first usage. This is particularly important for any application in which the stored materials upon contact with one another form a polymerized product.

The design of the coupling arrangement to permit the nozzle to be removable from the syringe becomes a critical factor for intermixing and dispensing viscous materials due to the mechanical limitations of the device for a given size discharge orifice and to the back pressure created by the tortuous route which the viscous materials are forced, under pressure, to follow through the static mixing element in the discharge nozzle. Accordingly, the coupling between the orifice end of the syringe and the nozzle assembly must be secure enough to withstand the hydraulic pressure developed in the device to dispense the materials from the syringe through the nozzle assembly. It is equally important that the coupling not only interlock the syringe to the nozzle, but that it also form a pressure seal to prevent any leakage of material at the interlock.

The multiple barrel dispensing device of the present invention overcomes the shortcomings of prior art multiple barrel dispensing devices and permits a much wider range of viscous and/or non-viscous materials to be intermixed. The nozzle assembly is readily removed from the syringe permitting reuse of the dispenser by substitution of a new nozzle.

SUMMARY OF THE INVENTION

A dispensing device for intermixing at least two materials and for dispensing the mixed product in a preferred volumetric ratio comprising:

a syringe having a plurality of elongated storage compartments for independently storing the materials to be intermixed and a common head having a separate channel extending from each compartment for discharging the stored materials from a common discharge end of said head;

a nozzle assembly having a single nozzle with an elongated channel for dispensing the materials discharged from the syringe, a common static mixing element disposed in said elongated channel for intermixing the materials fed from said syringe; and means for removably coupling said nozzle to said syringe with said means comprising a plurality of lugs projecting from the head of said syringe in an arrangement for forming bayonet grooves having an axial disposition relative to the longitudinal axis of the syringe and a circumferential disposition, and a nozzle head for said nozzle assembly, with said nozzle head having a means for engaging said bayonet grooves in the head of said syringe to form an interlock between said syringe and said nozzle, and means for forming a seal around said common discharge end of the head of said syringe simultaneously with the formation of said interlock to prevent leakage when material is being discharged from said device.

BRIEF DESCRIPTION OF THE DRAWINGS

The configurations which best illustrate the invention are shown in the accompanying drawings, which are to be considered as exemplary rather than limiting, and wherein:

FIG. 1 is a cross-sectional view of the dispensing device of the present invention;

FIG. 2 is a cross-sectional view of the nozzle assembly of FIG. 1 and a partial view, in perspective, of the head of the syringe of FIG. 1 shown spaced apart from the nozzle assembly;

FIG. 3 is an exploded perspective view of the preferred embodiment for the dispenser of FIG. 1;

FIG. 4 is an enlarged top view of the dispenser of FIG. 3, taken along the lines 4—4 of FIG. 3;

FIG. 5 is an end view of the nozzle in FIG. 3, taken along the lines 5—5 of FIG. 3; and FIG. 6 is an enlarged view, in cross-section, of an alternate embodiment of the invention, showing the head of the nozzle assembly and a variation in the head of the syringe.

DETAILED DESCRIPTION OF THE INVENTION

Referring now to FIGS. 1 and 2, in which the dispensing mixer of the present invention, identified by the reference numeral 10, is shown comprising a syringe (12) and a removable nozzle assembly (14). The syringe (12) is formed from any moldable plastic composition, preferably polyethylene or polypropylene, having two compartments (15) and (16) for separately storing materials to be combined, intermixed and discharged from the nozzle assembly (14). The compartments (15) and (16) may be of any configuration, preferably cylindrical and of different diameters although in the embodiment of FIG. 1, they are shown of equal size with each having an equal and predetermined fixed volume. The storage compartments (15) and (16) are adapted to be filled with any material composition of any desired viscosity based on the application for the mixed product. By using different size compartments, the volumetric ratio can be changed.

The stored materials are sealed in their respective compartments by pistons (17) and (18) which, in turn, are driven simultaneously by any conventional drive mechanism such as a pair of plungers (19) and (29). The plungers (19) and (29) are coupled together to be driven in unison using, e.g., a conventional double-barreled ratchet-type dispensing gun (not shown), which may be actuated mechanically, automatically, or using a hand-activated double plunger.

Each of the storage compartments (15) and (16) individually egress through channels (21) and (22), respectively, in the head (20) of the syringe (12). Upon applying pressure to the pistons (17) and (18), the impression material is expelled in common through the head (20) of the syringe (12). The passageways or channels (21) and (22) in the head (20) are relatively large openings which are separated by a common partition wall (23) which extends from and separates the compartments (15) and (16) from one another. A pair of thin diaphragm membranes (24) and (25) may be molded into the discharge openings (21) and (22) at the discharge end of the syringe (12) to close off each of the discharge openings (21) and (22). The membranes (24) and (25), as is more clearly shown in FIG. 3, are normally closed members which readily open in response to a predetermined minimum driving force applied to each compartment from the plungers (17) and (18), respectively. The diaphragm members (24) and (25) preferably include score lines (26) which are hinged at their outer radius to facilitate their opening.

The nozzle assembly (14) includes a head (30), a nozzle (32) having an elongated central bore or channel (34), and a static mixing element (36). The head (30) has a conically-shaped area (33) extending into the channel (34) of the nozzle (32). The conically-shaped area (33) functions as a funnel for guiding impression material into the elongated channel (34) and forms a conically-shaped wall (37) against which the static mixer (36) is seated. The conical area (33) also provides a pressure gradient between the high pressure output at the discharge end of the syringe and the back pressure at the entrance to the channel (34). The channel (34) of the nozzle (32) extends to a discharge orifice (38) at the distal end of the channel (34). The discharge orifice (38) has a relatively smaller diameter compared to the diameter of the channel (34) to retain the mixer (36) in the nozzle (32).

The static mixer (36) in the nozzle assembly (14) in a conventional mixing element consisting of a multiple number of serially arranged blades which have a bow tie-like configuration. A head (40) having a tapered contour conforming to the conical wall surface (37) is formed at the proximal end of the mixer (36) for engaging the conical wall (37). It is now well known that if a static mixer (36) is held in a stationary position in a nozzle, it will cause substantial intermixing of any two component fluids when forced through such nozzle.

The static mixer (36) is arbitrarily inserted and positioned into the channel (34) of the nozzle (32) with its head (40) seated against the conical walls (37) of the nozzle (32) in relatively tight engagement.

The head (20) of the syringe (12) is preferably of cylindrical geometry, molded with a plurality of lugs (50), preferably four, projecting in a symmetrical arrangement about its periphery in an evenly spaced relationship. The lugs (50) form bayonet grooves (52) which are used to removably couple the syringe (12) to the nozzle assembly (14). The bayonet grooves (52) have an axial component-directed parallel to the longitudinal axis of the syringe and a circumferential component. The head (30) of the nozzle assembly (14) has a bore (53) and a plurality of tong-like projections (54) corresponding to the number of lugs (50) about the head (20) of the syringe (12). The tong-like projections (54) extend radially inwardly from the head (30) into the bore (53) and are adapted to be inserted in the bayonet grooves (52) for forming an interlock between the head (20) of the syringe (12) and the head (30) of the nozzle assembly (14).

The head (30) of the nozzle assembly (14) is first advanced longitudinally relative to the head (20) of the syringe (12) so as to direct the tong-like projections (54) axially into the bayonet grooves (52) and is then rotated about the head (20) of the syringe (12) to twist the tong-like projections (54) circumferentially. Each of the lugs (50) have an inclined surface (55) to guide the tong-like projections (54) in the circumferential direction, as well as to move the tong-like projections (54) further along axially, and an end surface (58) which prevents further rotation. The tong-like projections (54) are tightened by twisting them into engagement with the end surface (58).

To insure against leakage at the interlocking juncture, a protruding bead (60) of preferably annular geometry is formed around the wider end of the conically-shaped area (33) in the head (30) of the nozzle (12). The bead (60) extends longitudinally into the bore (53) and is adapted to engage the head (20) when the tong-like projections are fully rotated into engagement with the end surfaces (58) of the lugs (50). The bead (60) may engage a corresponding flat surface (62) surrounding the openings (21) and (22) at the discharge end of the head (20). Alternatively, a washer-like gasket (64) of a relatively soft plastic composition, wax or rubber composition may be interposed between the flat surface (62) and the protruding shoulder (60) to form a seal when the nozzle is attached to the syringe (12). The washer-like member (64), if used, compensates for variations in tolerance during the molding operation and for irregularities in the surface (62) to assure effective engagement with the bead (60).

An alternative embodiment is shown in FIG. 6. The bead (60) is shown in an exaggerated form for purposes of illustration. A groove (65) is formed in the head (20) of the syringe (12) to form a "tongue and groove" coupling upon insertion of the bead (60). With this arrangement, a washer-like member (64) is clearly not needed. The diaphragm members (24) and (25) also contain notched ends (67) and (69) approximate the partition wall (23) to further facilitate opening of the diaphragms (24) and (25) upon the application of pressure by the plungers (17) and (18), as shown in FIG. 1.

The nozzle (32) may contain a plurality of wing-like elements (70) to permit the user of the device to readily grasp the nozzle (32) for removal from the syringe (12).

What we claim is:

1. A dispensing device for intermixing at least two viscous materials and for dispensing the mixed product in a preferred volumetric ratio comprising:

a syringe having a plurality of elongated storage compartments for independently storing the materials to be intermixed and a common head having a separate channel extending from each compartment for discharging the stored materials from a common discharge end of said head;

a nozzle assembly having a head and a single nozzle with an elongated channel forming an opening for dispensing the materials discharged from the syringe, a common static mixing element disposed in said elongated channel for intermixing the materials fed from said syringe, with the head of said nozzle having a bore and a conically shaped area extending from said bore into said elongated channel to receive said static mixing element; and means for removably coupling the head of the nozzle to the head of said syringe with said means comprising; a plurality of lugs projecting from the head of said syringe in an arrangement for forming bayonet grooves having an axial disposition relative to the longitudinal axis of the syringe and a circumferential disposition, tong-like projections surrounding the bore in said nozzle head for engaging said bayonet grooves in the head of said syringe to form an interlock between said syringe and said nozzle, and a protruding annular bead disposed in said nozzle rearward of the tong-like projections at the entrance to the conically shaped area for forming a seal upon engaging the head of said syringe simultaneously with the formation of said interlock and to prevent leakage when viscous material is being discharged from said device.

2. A dispensing device, as defined in claim 1, further comprising means for driving the materials from said storage compartments under pressure.

3. A dispensing device, as defined in claim 2, wherein said head of said syringe has a flat surface surrounding said common discharge end for engaging said annular bead.

4. A dispensing device, as defined in claim 2, wherein said head of said syringe has an annular groove for engaging said annular bead to form a tongue-and-groove seal.

5. A dispensing device, as defined in claim 2, further comprising a washer-like member for interposing between said annular bead and said head of said syringe to form a seal.

6. A dispensing device, as defined in claim 2, wherein said plurality of tong-like projections extend radially inward into said bore in said nozzle.

* * * * *